United States Patent [19]

Catt et al.

[11] Patent Number: 5,496,847
[45] Date of Patent: Mar. 5, 1996

[54] AMINOMETHYL-BENZODIOXANE AND BENZOPYRAN SEROTONERGIC AGENTS

[75] Inventors: John D. Catt, Southington; Ronald J. Mattson, Meriden, both of Conn.

[73] Assignee: Bristol-Myers Squibb Co., New York, N.Y.

[21] Appl. No.: 378,116

[22] Filed: Jan. 24, 1995

Related U.S. Application Data

[63] Continuation of Ser. No. 136,521, Oct. 14, 1993, Pat. No. 5,391,570.
[51] Int. Cl.$^6$ ............... A61K 31/335; A61K 31/36; C07D 319/20
[52] U.S. Cl. .................. 514/452; 514/450; 549/350; 549/366
[58] Field of Search ............... 549/350, 366; 514/450, 452

[56] References Cited

U.S. PATENT DOCUMENTS

| | | |
|---|---|---|
| 2,979,508 | 4/1961 | Janssen . |
| 3,717,634 | 2/1973 | Wu et al. . |
| 3,965,180 | 6/1976 | Lednicer . |
| 4,831,034 | 5/1989 | Barreau et al. . |
| 4,933,453 | 6/1990 | Hrib et al. . |
| 4,954,502 | 9/1990 | Smith et al. . |
| 4,957,921 | 9/1990 | Caprathe et al. . |
| 4,975,445 | 12/1990 | Caprathe et al. . |
| 5,168,099 | 12/1992 | Iwata et al. . |

OTHER PUBLICATIONS

J. S. New, "The Discovery and Development of Buspirone: a New Approach to the Treatment of Anxiety", *Medicinal Research Reviews*, 10, No. 3, (1990) pp. 283–326.

Primary Examiner—Nicky Chan
Attorney, Agent, or Firm—Sandra M. Nolan

[57] ABSTRACT

Certain aminomethyl-benzodioxanes and benzopyrans are useful serotonergic agents. They possess anxiolytic properties with few of the side effects often associated with dopaminergic agents.

8 Claims, No Drawings

AMINOMETHYL-BENZODIOXANE AND BENZOPYRAN SEROTONERGIC AGENTS

This is a continuation application of copending application Ser. No. 08/136,521, filed on Oct. 14, 1993, now U.S. Pat. No. 5,391,570.

BACKGROUND

This invention generally pertains to aminomethyl-benzodioxane and benzopyran compounds having anxiolytic, antidepressant and other psychotropic, bio-affecting properties and to their preparation and use.

In some preferred embodiments, the invention is concerned with 1,3-benzodioxo-5-yl-4-hydroxyclohexyl or 1,3-benzodioxo-5-yl-4-methoxy-cyclohexyl derivatives of these compounds. These compounds, and others structurally related thereto, possess a unique serotonergic profile that makes them useful in the treatment of anxiety and depression.

Lednicer discloses, in U.S. Pat. No. 3,965,180, a series of tranquilizers of Formula A. Formula A is:

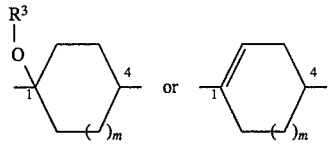

wherein:

$R_a$ is lower alkyl, halogen, trifluoromethyl or lower alkoxy;

$R_b$ is H or R;

$R_c$ is lower alkyl, $R_d$ is H or lower alkyl, and $R_e$ is H, lower alkyl or substituted aroylalkyl.

The bonds linking the benzene ring and/or $R_cO$ with the cyclohexene ring may have cis, trans or mixed configurations.

As can be seen, these earlier compounds are chemically distinguishable from the instant compounds on the basis of their chemical structures because they are alkyl-, halo-, halomethyl or alkoxybenzyl cyclohexanes, whereas the instant compounds are benzodioxo- or benzodioxanyl-cyclohexanes. Furthermore, neither $R_d$ nor $R_e$ in Lednicer's structure may be aminomethyl-benzopyran or aminomethyl-benzodioxane residues, as applicants' Formula I (below) requires.

All publications referred to herein are hereby incorporated by reference.

DESCRIPTION OF THE INVENTION

In its broadest aspect, the invention is concerned with certain compounds which are substituted aminomethyl-benzodioxanes and benzopyrans. The compounds, which are useful anxiolytic and antidepressant agents, conform to Formula I:

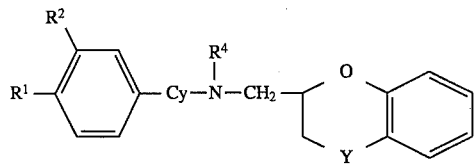

wherein:

$R^1$ and $R^2$ are both halogen or, taken together, form a —O—$(CH_2)_n$—O—bridge (n=1, 2 or 3);

Cy is either

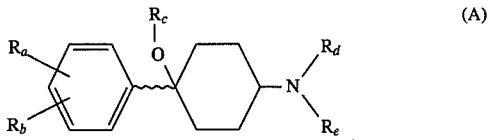

(m=0,1 or 2), with the phenyl substituent at the 1 position of the cycloalkanyl or cycloalkenyl ring and the amino substituent at the 4 position;

$R^3$ and $R^4$ are independently H or $C_{1-4}$alkyl; and

Y is O, $CH_2$, or S.

Compounds of Formula I include all pharmaceutically acceptable salts and/or solvates thereof. The invention also encompasses all stereoisomers of compounds of Formula I.

Pharmaceutically acceptable salts, amides and hydrates based on Formula I can be obtained using inorganic or organic acids such as sulfuric, phosphoric, hydrochloric, hydrobromic, hydroiodic, citric, acetic, benzoic, fumaric, cinnamic, mandelic, nitric, mucic, isethionic, palmitic, heptanoic and the like. Fumarate and hemifumarate salts are highly useful, as are acetates and hydrates.

While $R^1$ and $R^2$ may both be halogen or taken together are —O—$(CH_2)_n$—O—, wherein n is 1, 2, or 3, it is generally preferred that $R^1$ and $R^2$ are both fluorine or that they are parts of a ring in which n is 1.

While Cy may be either a cycloalkanyl or a cycloalkenyl linkage, the cycloalkanyl linkage is highly preferred. It is also preferred that m be 1.

While $R^3$ and $R^4$ may both be hydrogen or $C_{1-4}$moieties, it is generally preferred that only one of them be alkyl. Preferred alkyl groups are those that contain not more than two carbon atoms. Thus, methyl and ethyl groups are preferred embodiments for $R^3$ or $R^4$, when either is not hydrogen.

n is the integer 1, 2 or 3. In preferred embodiments, n is 1 or 2. In highly preferred embodiments, n is 1.

Y may be O, $CH_2$, N or S. In preferred embodiments, Y is O or $CH_2$, with O being highly preferred.

Preferred compounds of Formula I are:

Cis-4-[(2S-1,4-benzodioxan-2-yl)methylamino]-1-(1,3-benzodioxol-5-yl )cyclohexanol;

Cis-N-[4-(1,3-benzodioxol-5-yl)-4-methoxycyclohexyl]-2S-1,4-benzodioxane-2-methanamine hemifumarate;

(±)-Cis-4-[[(1,4-benzodioxan-2-yl)methyl]amino]-1-(1, 3-benzodioxol-5-yl)cyclohexanol hydrate;

(±)-Cis-N-[4-(1,4-benzodioxan-6-yl)-4-methoxycyclohexyl]-1,4-benzodioxane-2-methanamine hemifumarate;

(±)-Cis-N-[4-(1,3-benzodioxol-5-yl)-4-ethoxycyclohexyl]-1,4-benzodioxane-2-methanamine fumarate;

(±)-Cis-N-[4-(1,3-benzodioxol-5-yl)-4-methoxycyclohexyl]-1,4-benzodioxane-2-methanamine hemifumarate;

(±)-Cis-N-ethyl-N-[4-(1,3-benzodioxol-5-yl )-4-hydroxycylohexyl]-1,4-benzodioxane-2-methanamine fumarate;

(±)-Cis-N-methyl-N-[4-(1,3-benzodioxol-5-yl)-4-methoxycyclohexyl]-1,4-benzodioxane-2-methanamine fumarate;

(−)-(R)-Cis-N-[4-(1,3-benzodioxol-5-yl)-4-methoxycyclohexyl]-1,4-benzodioxane-2-methanamine fumarate;

(±)-Trans-N-[4-(1,3-benzodioxol-5-yl)-4-methoxycyclohexyl]-1,4-benzodioxane-2-methanamine hemifumarate;

(±)-Cis-4-[[(3,4-dihydro-2H-1-benzopyran-2-yl)methyl]amino]-1(1,3-benzodioxol-5 -yl)cyclohexanol;

N-[4-(1,3-benzodioxol-5-yl)-3-cyclohexen-1-yl]-2S-1,4-benzodioxane-2-methanamine; and (±)-Cis-4-[(1,4-benzodioxan-2-yl)methylamino]-1-(3,4-difluorophenyl)cyclohexanol.

Another aspect of the present invention is a method for treating a mammal afflicted with anxiety or panic disorders which comprises administering systematically to said mammal a therapeutically effective amount of a compound of Formula I or a pharmaceutically acceptable add addition salt, amide, hemihydrate, or hydrate thereof.

The dosage regimen must in each case be carefully adjusted, utilizing sound professional judgment and considering the age, weight and condition of the recipient, the route of administration and the nature and gravity of the illness. Generally, the daily dose will be from about 0.01 to about 10 mg/kg, preferable 0.1 to 2 mg/kg, when administered parenterally and from about 1 to 50 mg/kg, when administered orally. In some instances, a sufficient therapeutic effect can be obtained at lower doses while in others, greater doses will be required.

Systemic administration refers to oral, rectal, transnasal, transdermal, and parenteral (i.e., intramuscular, intravenous, and subcutaneous) routes. Generally, when a compound is administered orally, a greater quantity of the active agent is required to produce the same effect as a similar quantity given parenterally. In accordance with good clinical practice, it is preferred to administer the present compounds at a concentration level that will produce effective anxiolytic effects without causing any harmful or untoward side effects.

The compounds of the present invention may be administered for anxiolytic purposes, either as individual therapeutic agents or in mixtures with other therapeutic agents. Therapeutically, they are generally given as pharmaceutical compositions comprised of an anxiolytic amount of a compound of Formula I or a pharmaceutically acceptable derivative thereof and a pharmaceutically acceptable carrier. Pharmaceutical compositions which provide from about 1 to 500 mg of the active ingredient per unit dose are preferred and are conventionally prepared as tablets, lozenges, capsules, powders, aqueous or oily suspensions, syrups, elixirs, and aqueous solutions.

The nature of the pharmaceutical composition employed will, of course, depend on the desired route of administration. For example, oral compositions may be in the form of tablets or capsules and may contain conventional excipients such as binding agents (e.g., starch) and wetting agents (e.g., sodium lauryl sulfate). Solutions or suspensions of one or more Formula I compounds with conventional pharmaceutical vehicles are employed for parenteral compositions, such as aqueous solutions for intravenous injection or oily suspensions for intramuscular injection.

The reaction schemes and biological data set out hereafter refer to a sampling of the compounds of the invention.

PREPARATION

The intermediate ketones, i-a and i-b, are prepared as shown below. Reaction of cyclohexan-1,4-dione mono-ethyleneketal with organometallic reagents, such as Grignard reagents, aryl lithium reagents and the like, furnish the 4-aryl-4-hydroxy-cyclohexanone ketals, ii. These reactions are generally carried out in solvents such as tetrahydrofuran, diethyl ether, dimethoxyethane, dioxane, ethylene glycol dimethylether and the like at temperatures from −80° to 30° C. The ketals are cleaved under acidic conditions in a solvent such as methanol, ethanol, 2-propanol, acetone, tetrahydrofuran, dioxane, dimethoxyethane, acetonitrile, dichloromethane, 1,2-dichloroethane and the like to give the 4-aryl-4-hydroxycyclohexanones, i-a. Acids suitable for this hydrolysis include but are not limited to hydrochloric, sulfuric, acetic, phosphoric, para-toluenesulfonic, methanesulfonic, benzoic and the like.

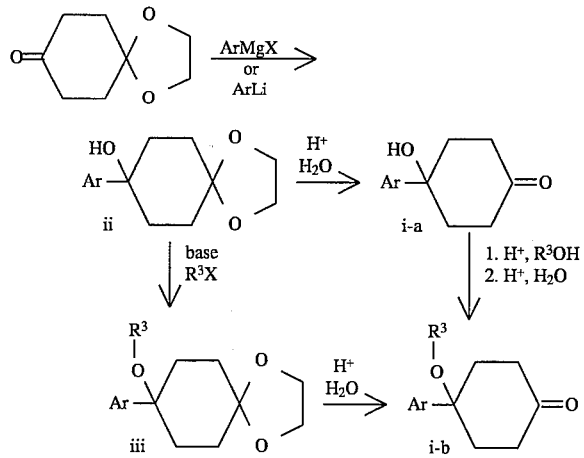

The hydroxycyclohexanones, i-a, can be reacted in an alcoholic solution with a strong acid such as sulfuric acid, p-toluene sulfonic acid, or the like, followed by mild acidic hydrolysis as described above to give the alkoxycyclohexanones, i-b. Alternatively the cyclohexanols, ii, can be reacted with an alkylating agent and an appropriate base in a suitable solvent such as tetrahydrofuran, diethyl ether, dimethylformamide, dimethylacetamide, dimethyl sulfoxide, dioxane, dimethoxyethane, ethylene glycol dimethyl ether and the like to give the ethers, iii. Appropriate bases for this reaction include but are not limited to sodium hydride, potassium hydride, calcium hydride, lithium hydride, sodium carbonate, potassium carbonate, sodium hydroxide, potassium hydroxide, calcium hydroxide, butyl lithium, methyl lithium, phenyl lithium and the like. Alkylating agents include, but are not limited to, methyl iodide, ethyl iodide, dimethyl sulfate, diethyl sulfate, propyl iodide, propyl bromide, methyl trifluoro-methanesulfonate, ethyl trifluoromethanesulfonate, methyl trifluoroacetate, ethyl trifluoroacetate, and the like. Further mild acidic hydrolysis of iii by the methods described above yields the alkoxycyclohexanones, i-b.

The aminomethyl-benzopyran, iv-a (Y=CH$_2$), was prepared from the corresponding carboxylic acid, v, in 4 steps as shown below. The acid, v, may be reduced to the alcohol with a suitable reducing agent, such as LiAlH$_4$, AlH$_3$, B$_2$H$_6$, or the like. The intermediate alcohol is then activated by conversion to the alkyl halide, sulfonate ester, or the like, to give intermediate vi. Subsequent reaction of vi under standard conditions with azide, followed by hydrogenation over a catalyst such as palladium on carbon, provides the aminomethylbenzopyran, iv-a (Y=CH$_2$). Alternatively, vi can be used to alkylate an imide such as phthalimide, succinimimde or the like. Subsequent cleavage of the imide using reagents such as hydrazine or sodium hydroxide also provides the aminomethyl-benzopyran, iv-a (Y=CH$_2$). Both optical isomers of the aminomethyl-benzodioxane fragment, iv-b (Y=O), were steriospecific synthesized by the method of Nelson and Wennerstrom(*J.Med. Chem*, 1977, 20, 880).

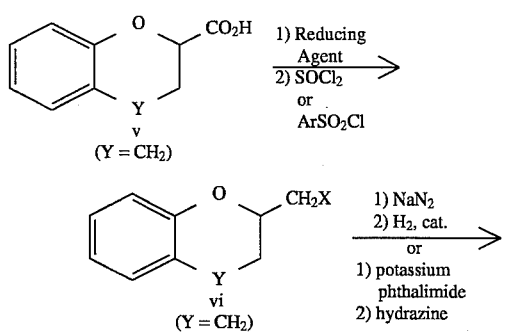

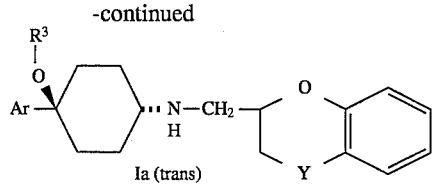

The N-alkyl groups, $R^4$, may be reductively added to compounds of Formula I using aldehydes and ketones with reducing agents such as those described above. Alternatively the N-alkyl groups can be added by simple alkylation using alkylating agents and an appropriate bases in suitable solvents such as those described above.

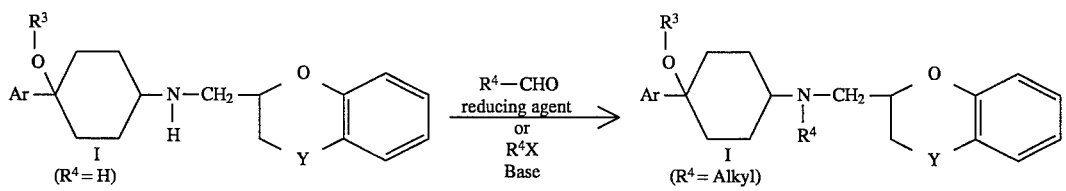

-continued

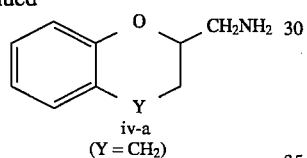

The cyclohexanones, i, may be reductively coupled with the amines, iv, to provide the compounds of Formula I as a mixture of cis and trans cyclohexane isomers which can be separated by methods known to those skilled in the art, such as chromatography, recrystallization, and the like. Reagents suitable for this reductive coupling include but are not limited to sodium borohydride, sodium cyanoborohydride, sodium triacetoxyboro-hydride, sodium borohydride/titanium isopropoxide, sodium cyanoborohydride/titanium isopropoxide and the like. The reductively coupling is generally run in a solvent such as ethanol, methanol, tetrahydrofuran, dioxane, dichloromethane, 1,2-dichloroethane, dimethoxyethane, and the like, at temperatures of 25° to 100° C. A preferred method of coupling the two fragments, i and iv, consists of refluxing them in a solvent such as benzene, toluene, or cyclohexane, until the elimination of water is complete. Subsequent reduction with sodium borohydride in alcoholic solvents yields essentially all cis-cyclohexane product, Ia (cis).

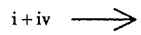

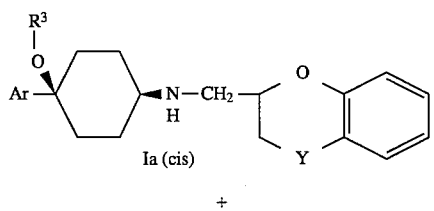

Treatment with strong acid converts the cyclohexanols and cyclohexyl ethers of Formula I to the corresponding cyclohexenes (Ib) as shown below. Alternatively, reagents such as $POCl_3$, $SOCl_2$, or the like, in solvents such as, e.g., pyridine, may also be used for this conversion.

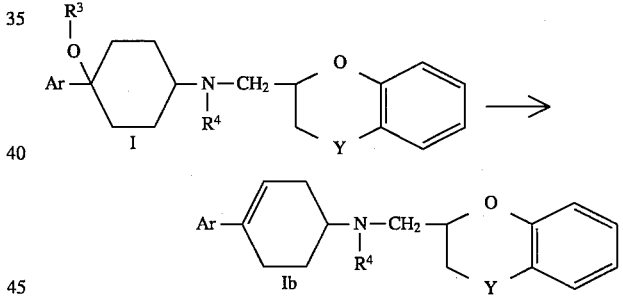

EXAMPLES

The compounds which constitute this invention, their methods of preparation and their biological actions will be better appreciated after consideration of the following examples, which are given for the purpose of illustration only and are not be construed as limiting the invention. In the following examples, temperatures are expressed in degrees Celsius (° C.) and melting points are uncorrected. Unless stated otherwise, all percentages given herein are weight percentages based on total composition weight.

The following examples describe in detail the preparation of compounds of Formula I, as well as Formula II synthetic intermediates in each process. It will be apparent to those skilled in the art that modifications, both of materials and methods, will allow preparation of other compounds disclosed herein.

A. Preparation of intermediate compounds

Some representative procedures for preparation of synthetic intermediate compounds utilized above are given herein below. Most starting materials and certain intermediates are either commercially available or procedures for their synthesis are readily available in the chemical literature, allowing their full utilization by one skilled in the art of organic synthetic chemistry.

Intermediate 1:
8-(1,3-Benzodioxol-5-yl)-1,4-dioxaspiro[4.5]decan-8-ol

A solution of 1,4-cyclohexanedione monoethylene ketal (31.2 g, 0.2 mole) in 100 ml dry THF was added to a −60° C. solution of the Grignard reagent prepared from magnesium metal (7.2 g, 0.3 mole) and 5-bromo-1,3-benzodioxole (60.3 g, 0.3 mole). The mixture was allowed to warm to 25° C. and quenched with saturated $NH_4Cl$ and extracted with ether. The extracts were dried with $Na_2SO_4$ and the solvent removed in vacuo. The residue was crystallized from isopropyl ether to give the product (47.5 g, 85%, m.p: 103°–104° C.).

Intermediate 2:
4-(1,3-benzodioxol-5-yl)-4-hydroxycyclohexanone

A solution of 8-(1,3-benzodioxol-5-yl)-1,4- dioxaspiro [4.5]decan-8-ol (IIIb; 5 g, 18 mmole) in 75 ml acetone, 1 ml 12N HCl, and 50 ml water, was stirred for 2 hr. After dilution with an additional 50 ml water the solid was collected to give the product (4.0 g, 95%, mp: 166°–168° C.).

Intermediate 3:
4-(1,4-benzodioxan-6-yl)-4-hydroxycyclohexanone

A solution of 1,4-cyclohexanedione monoethylene ketal (7.8 g, 50 mmole) in 50 ml dry THF was added to a of the Grignard reagent prepared from magnesium metal (1.34 g, 55 mmole) and 6-bromo-1,4-benzodioxane (10.75 g, 50 mmole). The mixture was stirred for 16 hr, quenched with saturated $NH_4Cl$ and extracted with ether. The ether extracts were dried with $Na_2SO_4$ and the solvent removed in vacuo. Acetone (75 ml) and 1N HCl (75 ml) were added and the solution was stirred 18 hr to give a tan precipitate which was filtered and air dried (6.38 g, 59.1%). This material was used without further purification.

Intermediate 4:
4-(1,3-Benzodioxol-5-yl)-4-methoxycyclohexanone

A solution of 8-(1,3-Benzodioxol-5-yl)-1,4-dioxa-spiro [4.5]decan-8-ol (5.0g, 1.8 mmole) in 100 mL methanol with 1 mL conc. hydrochloric acid was stirred for 22 hr and the solution concentrated in vacuo. The residue was purified by chromatography on silica eluting with ethyl acetate-hexane (1:19) to give the product (70%, mp: 84°–85° C.).

Calc'd for $C_{14}H_{16}O_4$: C, 67.73%; H, 6.50%. Found: C, 67.25%; H, 6.56%.

Intermediate 5:
8-(3,4-Difluorophenyl)-1,4-dioxaspiro[4.5]decan-8-ol

This compound was prepared from 1,4-cyclohexanedione monoethylene ketal (15.6 g, 100 mmole) and 3,4-difluorophenyl magnesium bromide (100 mmole) in the usual mariner. The crude product was crystallized from isopropyl ether to give the product (42%, mp: 118°–120° C.).

Calc'd. for $C_{14}H_{16}F_2O_3$: C, 62.22%; H,5.97%. Found: C, 61.97%; H, 6.35%.

Intermediate 6:
4-(3,4-Difluorophenyl)-4-hydroxycyclohexanone

A solution of 8-(3,4-difluorophenyl)-1,4- dioxaspiro[4.5] decan-8-ol (5.4 g, 20 mmole) in acetone-1N hydrochloric acid (1:1) was stirred for 4 hr. The acetone was removed in vacuo and the crude material crystallized from isopropyl ether to give the product (62%, mp: 84°–85° C.).

Calc'd. for $C_{12}H_{12}F_2O_2$: C, 63.72%; H, 5.35%. Found: C, 62.72%; H, 5.24%.

Intermediate 7:
(±)-[(3,4-dihydro-2H-1-benzopyran-2-yl)methyl]amine

LAH pellets (3.2 g, 84.3 mmole) were added slowly to a stirred solution of 3,4-dihydro-2H-1-benzopyran-2-carboxylic acid (15 g, 84.3 mmole) in THF (150 ml). After the vigorous reaction subsided, the mixture was refluxed for 1 hr and then cooled. To the hot mixture were added sequentially, $H_2O$ (3.2 ml), 15% NaOH (3.2 ml), and then $H_2O$ (12.8 ml). The mixture was filtered and the filter cake washed with THF. The THF filtrate was concentrated in vacuo, and Kügelrohr distilled to a clear oil (13.85 g, 100%). This alcohol intermediate was stirred in $SOCl_2$ for 18 hr. The excess $SOCl_2$ was removed in vacuo and the resulting dark oil was Kügelrohr distilled to a clear oil (8.65 g, 56.2%). This alkyl chloride intermediate was heated to 100° in DMF with $NaN_3$ (4.32 g, 66 mmole) and KI (0.2 g) for 72 hr. The mixture was diluted with $H_2O$ (250 ml) and extracted with $CH_2Cl_2$ three times. The $CH_2Cl_2$ extracts were concentrated in vacuo. The residue was hydrogenated at 60 psi over 10% Pd/C (1 g) in ethanol and 37% HCl (10 ml) for 3 hr. $H_2O$ (20 ml) was added and the mixture was filtered. The ethanol was removed in vacuo and the aqueous residue was made basic with 10N NaOH. The mixture was extracted three times with ethyl acetate (50 ml portions). The extracts were concentrated in vacuo and the tan oil was Kügelrohr distilled to a dear oil (6.35 g, 82.2%). The product was used without further purification.

B. Preparation of Compounds of Formula I

EXAMPLE 1

Cis-4-[(2S-1,4-Benzodioxan-2-yl)methylamino]-1-(1,3-benzodioxol-5-yl)cyclohexanol A mixture of 2S-aminomethyl-1,4-benzodioxane (1.4 g, 8.5 mmole) (J. B. Stenlake, *J. Pharm. Pharmac.,* 1968, 20; Suppl., 82S), 6-(1,3-benzodioxol-5-yl)-6-hydroxycyclohexanone (2.0 g, 8.5 mmole) and titanium isopropoxide (5 ml) was warmed slightly until a dear mix formed. After stirring for 2 hr no carbonyl absorption was observed in the IR and the mix was dissolved in ethanol (50 ml). Sodium borohydride (0.4 g, 10 mmol) was added and the mixture stirred for 4 hr. The mixture was hydrolyzed with 15% NaOH solution (20 ml). The insolubles were removed and the solution concentrated in vacuo. The residue was dissolved in ether and the solution washed with 1N HCl. The add washes were basified with NaOH solution and the basic mixture extracted with methylene chloride. The extracts were dried over sodium sulfate and concentrated in vacuo. The residue was crystallized from ether to give the product as a white solid (81%, mp: 110°–111° C.).

Calc'd for $C_{22}H_{25}NO_5$: C, 68.92%; H, 6.58%; N, 3.66%. Found: C, 69.03%; H, 6.65%; N, 3.72%.

EXAMPLE 2

Cis-N-[4-(1,3-Benzodioxol-5-yl)-4-methoxycyclohexyl]
-2S-1,4-benzodioxane-2-methanamine
hemifumarate A mixture of titanium isopropoxide (3.5 ml), 6-(1,3-benzodioxol-5-yl)-6-methoxycyclohexanone (1.23 g, 4.96 mmole) and 2S-aminomethyl-1,4-benzodioxane (0.82 g, 4.96 mmole) was warmed for 1 hr. The melt was dissolved in ethanol (50 ml) and sodium borohydride (0.6 g, 15 mmol) was added. After stirring for 18 hr the mixture was hydrolyzed with 15% NaOH solution and the insolubles removed and washed with acetone. The solution was concentrated in vacuo and the residue purified by chromatography on silica eluting with methanol in methylene chloride (2%) to give 1.1 g of product as an oil. The material was dissolved in acetone and fumaric acid (0.32 g) was added to give the fumarate salt (56%, top: 208°–209° C.).

Calc'd for $C_{23}H_{27}NO_5 \cdot 0.5\ C_4H_4O_4$: C, 65.93%; H, 6.42%; N, 3.08%. Found: C, 66.02%; H, 6.50%; N, 3.08%.

EXAMPLE 3

(±)-Cis-4-[[(1,4-benzodioxan-2-yl)methyl]amino]-1-(1,3-benzodioxol-5-yl)cyclohexanol hydrate.

This compound was prepared in a manner similar to that used in Example 1, using racemic starting material. This racemic product was purified by chromatography on silica gel using 5% methanol/ethyl acetate to give a white powder (47.4%, mp: 114°–116° C.).

Calc'd for $C_{22}H_{25}NO_5 \cdot 0.0.11H_2O$: C, 68.55%; H, 6.60%; N, 3.63%. Found: C, 68.55%; H, 6.54%; N, 3.58%.

EXAMPLE 4

(±)-Cis-N-[4-(1,4-benzodioxan-6-yl)-4-methoxycyclohexyl]-1,4-benzodioxane-2-methanamine
hemifumarate This compound was prepared in a manner similar to that used in Example 2, using racemic aminomethyl-1,4-benzodioxane and 4(1,4-benzodioxan-6-yl)-4-methoxycyclohexanone (prepared in a manner similar to Intermediate 4). The racemic product was purified by chromatography on silica gel using 5% methanol/ethyl acetate and then converted to the hemifumarate salt in acetonitrile to give a white powder (64.3%, mp: 201°–202.5° C.).

Calc'd for $C_{24}H_{29}NO_5 \cdot 0.5C_4H_4O_4$: C, 66.51%; H, 6.66%; N, 2.98%. Found: C, 66.46%; H, 6.69%; N, 2.94%.

EXAMPLE 5

(±)-Cis-N-[4-(1,3-benzodioxol-5-yl)-4-ethoxycyclohexyl]-1,4-benzodioxane-2-methanamine fumarate This compound was prepared in a manner similar to Example 2 using racemic aminomethyl-1,4-benzodioxane and 4-(1,3-benzodioxol-5-yl)-4-ethoxy-cyclohexanone (prepared in a manner similar to Intermediate 4). The racemic product was purified by chromatography on silica gel using 5% methanol/ethyl acetate and then converted to the fumarate salt in acetonitrile to give a white powder (46.6%, mp: 184°–195° C.).

Calc'd for $C_{24}H_{29}NO_5 \cdot 0.7\ C_4H_4O_4$: C, 65.32%; H, 6.51%; N, 2.84%. Found: C, 65.20%; H, 6.49%; N, 2.80%.

EXAMPLE 6

(±)-Cis-N-[4-(1,3-Benzodioxol-5-yl)-4-methoxycyclohexyl]-1,4-benzodioxane-2-methanamine hemifumarate A cyclohexane solution (50 ml) of 4-(1,3-benzodioxol-5-yl)-4-methoxycyclo-hexanone (2.48 g, 10 mmole) and racemic aminomethyl-1,4-benzodioxane (1.65 g, 10 mmole) were refluxed under a Dean-Stark trap for 2.5 hr. The solvent was removed in vacuo, and the crude imine washed with diisopropyl ether to give a white powder (3.33 g, 84.3%). The imine intermediate (3.00 g, 7.595 mmole) was dissolved in ethanol (30 ml) and then reduced for 18 hr with sodium borohydride (four 0.15 g tablets, 16 mmole). The ethanol was removed in vacuo and the residue dissolved in ethyl acetate. After extraction with water and saturated sodium carbonate, the ethyl acetate layer was concentrated in vacuo to give a light yellow oil. This crude product was converted to the hemifumarate salt in ethyl acetate to give a white powder (78.4%, mp: 202°–203° C.).

Calc'd for $C_{23}H_{27}NO_5 \cdot 0.5C_4H_4O_4$: C, 65.92%; H, 6.42%; N, 3.08%. Found: C, 66.12%; H, 6.41%; N, 3.08%.

EXAMPLE 7

(±)-Cis-N-Ethyl-N,[4-(1,3-benzodioxol-5-yl)-4-hydroxycyclohexyl]-1,4-benzodioxane-2-methanamine fumarate A solution of (±)-Cis-N-[4-(1,3-benzodioxol-5-yl)-4-methoxycyclohexyl]-1,4-benzodioxane-2 -methanamine (1.0 g, 2.245 mmole), sodium cyanoborohydride (0.62 g, 10 mmole), and acetaldehyde (2 ml, 36 mmole) in ethanol (15 ml) was stirred for 48 hr, and then refluxed for 2 hr. The reaction mixture was filtered and concentrated in vacuo. The residue was dissolved in ethyl acetate and extracted with water and brine. The ethyl acetate extract was concentrated in vacuo to give the crude oil which was purified by chromatography on silica gel using 5% to 20% methanol/ethyl acetate as the eluent to give a clear oil (0.86 g, 82.6%). This free base was dissolved in acetonitrile (40 ml) and 12N HCl (0.25 ml) was added to give the HCl salt as a white powder (0.66 g, 65.5% overall yield, mp: 181°–183.5° C.).

Calc'd for $C_{24}H_{29}NO_5 \cdot HCl$: C, 64.35%; H, 6.75%; N, 3.13%. Found: C, 64.75%; H, 6.75%; N, 3.27%.

EXAMPLE 8

(±) -Cis-N-Methyl-N-[4-(1,3-benzodioxol-5-yl)-4-methoxycyclohexyl]-1,4,-benzodioxane-2-methanamine fumarate (±)-Cis-N-[4-(1,3-benzodioxol-5-yl)-4-methoxycyclohexyl]-1,4-benzodioxane-2-methanamine was converted to this compound in a reaction similar to Example 7 using sodium cyanoborohydride and formaldehyde in ethanol. The crude oil was treated with fumaric acid in ethyl acetate, but a solid salt failed to form. The ethyl acetate was removed in vacuo, and the glassy product washed with ether. The product was partitioned between ethyl acetate and saturated sodium carbonate to give the free base. The ethyl acetate extract was concentrated in vacuo to a clear oil that solidified upon standing. This solid was recrystallized from 10% ethyl acetate/hexane to give a white powder (44.5%, mp: 114.5°–117° C.).

Calc'd for $C_{24}H_{29}NO_5$: C, 70.05%; H, 7.10%; N, 3.40%. Found: C, 70.04%; H, 7.09%; N, 3.38%.

EXAMPLE 9

(−)-(R)-Cis-N-[4-(1,3-benzodioxol-5-yl)-4-methoxycyclohexyl]-1,4-benzodioxane-2-methanamine fumarate This compound was prepared in a manner similar to Example 2 using 2R- aminomethyl-1,4-benzodioxane. The product was purified by chromatography on silica gel using 5–20% methanol/ethyl acetate to give a clear oil, which was converted to the hemifumarate salt as a white powder (27.9%, mp: 202°–203° C.).

Calc'd for $C_{23}H_{27}NO_5 \cdot 0.5C_4H_4O_4$: C, 65.92%; H, 6.42%; N, 3.08%. Found: C, 65.77%; H, 6.21%; N, 3.03%.

EXAMPLE 10

(±)-Trans-N-[4-(1,3-benzodioxol-5-yl)-4-methoxycyclohexyl]-1,4-benzodioxane-2-methanamine hemifumarate A solution of cyclohexane (35 ml), 4-(1,3-benzodioxol-5-yl)-4-methoxy-cyclohexanone (2.48 g, 10 mmole) and racemic aminomethyl-1,4-benzodioxane (1.65 g, 10 mmole) were refluxed under a Dean-Stark trap for 4 hr. The solvent was removed in vacuo, and the crude imine was dissolved in THF (40 ml) and then stirred for 3 days with sodium triacetoxyborohydride (3.40 g, 16 mmole). The solvent was removed in vacuo and the residue dissolved in ethyl acetate. After extraction with water and saturated sodium carbonate, the ethyl acetate layer was concentrated in vacuo to give a light yellow oil. This crude mixture of cis and trans cyclohexyl isomers was separated by chromatography on silica gel using 25–100% ethyl acetate/hexanes to give the less polar trans product (1.29 g, 37.6%) and the more polar cis product (1.36 g, 42.5%, previously described in Example 6). The less polar trans product was converted to the fumarate salt in methanol/ethyl acetate (mp: 171°–173° C.).

Calc'd for $C_{23}H_{27}NO_5 \cdot C_4H_4O_4$: C, 63.15%; H, 6.09%; N, 2.73%. Found: C, 63.07%; H, 6.04%; N, 2.65%.

EXAMPLE 11

(±)-Cis-4-[[(3,4-dihydro-2H-1-benzopyran-2-yl)methyl]amino]-1-(1,3-benzodioxol-5-yl)cyclohexanol This compound was prepared from (±)-[(3,4-dihydro-2H-1-benzopyran-2-yl)methyl]amine and 4-(1,3-benzodioxol-5-yl)-4-hydroxycyclohexanone in a manner similar to Example 1 to give the crude product. This racemic product was purified by chromatography on silica gel using 0–10% methanol/ethyl acetate to give a white powder (34.9%, mp: 135°–137° C.).

Calc'd for $C_{23}H_{27}NO_4$: C, 72.42%; H, 7.14%; N, 3.67%. Found: C, 72.13%; H, 7.10%; N, 3.69%.

EXAMPLE 12

N-[4-(1,3-Benzodioxol-5-yl)-3-cyclohexen-1-yl]-2S-1,4-benzodioxane-2-methanamine A solution of cis-N-[4-(1,3-benzodioxol-5-yl)-4-methoxycyclohexyl]-2S-1,4-benzo-dioxan-2-methanamine in etherethanol was acidified with conc HCl. A solid separated and was converted to the free base. The material was purified by chromatography on alumina eluting with ethyl acetate in hexane (1:4) to give the product (10%, mp: 90°–92° C.).

Calc'd for $C_{22}H_{23}NO_4 \cdot 0.5H_2O$: C, 71.60%; H, 6.40%; N, 3.80%. Found: C, 71.67%; H, 6.38%; N, 3.80%.

EXAMPLE 13

(±)-Cis-4-[(1,4-Benzodioxan-2-yl)methylamino]-1-(3,4-difluorophenyl)cyclohexanol A mixture of 1,4-benzodioxane-2-methanamine (0.5 g, 2.5 mmole), 4-(3,4-difluoro-phenyl)-4-hydroxycyclohexanone (0.56 g, 2.5 mmole) and titanium isopropoxide (0.9 ml, 3 mmole) in a minimum volume of dichloromethane was stirred under nitrogen. After stirring for 18 hr no carbonyl absorption was observed in the IR and the mixture was dissolved in ethanol (10 ml). Sodium borohydride (0.1 g, 2.5 mmol) was added and the mixture was stirred for 3 hr. The mixture was hydrolyzed with 15% NaOH solution (5 ml). The mixture was filtered and the filtrate concentrated in vacuo. The residue was dissolved in ether and the solution shaken with 1N HCl to give the product as the hydrochloride. The salt was collected and crystallized from 2-propanol/hexane (70%, top: 254°–256° C.).

Calc'd for $C_{21}H_{23}F_2NO_3 \cdot HCl$: C, 61.24%; H, 5.87%; N, 3.40%. Found: C, 61.12%; H, 5.85%; N, 3.36%.

BIOLOGICAL ACTIVITY

The biological activity of the compounds of the invention is demonstrated by the data in Table 1.

TABLE 1

5-HT$_{1A}$ Activity of Aminomethyl Benzodioxanes and Benzopyrans

| Example | 5-HT$_{1A}$ IC$_{50}$* |
|---|---|
| 1 | A |
| 2 | A |
| 3 | A |
| 4 | B |
| 5 | B |
| 6 | B |
| 7 | C |
| 8 | C |
| 9 | A |
| 10 | C |
| 11 | A |
| 12 | C |
| 13 | A |

*A: IC$_{50}$ < 1 nM; B: IC$_{50}$ = 1–5 nM; C: IC$_{50}$ = 5–25 nM.

In vitro IC$_{50}$ test values for binding to the 5-HT$_{1A}$ receptor were determined for representative compounds of Formula I by the method of S. J. Peroutka, *Brain Research* 344, 167 (1985); with only minor modifications. Test IC$_{50}$ values lower than 100 nM are considered to reflect activity at the 5-HT$_{1A}$ receptor. Compounds with IC$_{50}$ values lower than 25 nM comprise the preferred compounds.

The compounds comprising the present invention are selective agonists and partial agonists at the serotonergic 5-HT$_{1A}$ receptor. Serotonergic pathways are implicated in a variety of psychiatric disorders such as anxiety and depression. It is also known that partial agonists of the 5-HT$_{1A}$ receptor are clinically effective in the treatment of anxiety (see: D. P. Taylor, "Serotonin Agents in Anxiety," *Annals of the New York Academy of Sciences* vol. 600, entitled: "The Neuropharmacology of Serotonin," pp 545–557, Oct. 15, 1990.) Furthermore, there is evidence that 5-HT$_{1A}$ agents may be useful in the prophylactic treatment of migraine (see: J. Pascual and J. Berciano, "An Open Trial of Buspirone in Migraine Prophylaxis. Preliminary Report," *Clinical Neuropharmacology* 14:3, 1991, pp. 245–250). Compounds of the present invention are thus envisioned to be useful in the treatment of disorders such as anxiety, panic disorders, obsessive-compulsive disorder, and depression, as well as in the prophylactic treatment of migraine.

Reasonable variations, such as those which would occur to a skilled artisan, may be made herein without departing from the scope of the invention.

We claim:

1. A compound of Formula I or a pharmaceutically acceptable salt, amide or hydrate thereof:

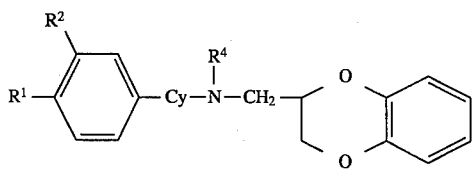

wherein:
R$^1$ and R$^2$ are both halogen or, taken together, form a —O—(CH$_2$)$_n$—O— bridge (n=1, 2 or 3);
Cy is either

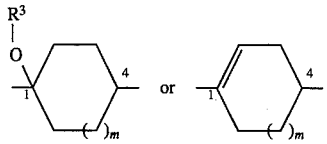

(m=0, 1 or 2), with the phenyl substituent at the 1 position of the cycloalkanyl or cycloalkenyl ring and the amino substituent at the 4 position; and
R$^3$ and R$^4$ are independently H or C$_{1-4}$alkyl.

2. The compound of claim 1 wherein n=1 or 2.

3. The compound of claim 2 wherein R is hydrogen, methyl or ethyl.

4. The compound of claim 3 wherein the compound is selected from:

Cis-4-[2S-1,4-benzodioxan-2-yl)methylamino]-1-(1,3-benzodioxol-5-yl)cyclohexanol;

Cis-N-[4-(1,3-benzodioxol-5-yl)-4-methoxycyclohexyl]-2S-1,4-benzodioxane-2-methanamine hemifumarate;

(±)-Cis-4-[[(1,4-benzodioxan-2-yl)methyl]-amino]-1-(1,3-benzodioxol-5-yl)cyclohexanol hydrate;

(±)-Cis-N-[4-(1,3-benzodioxan-6-yl)-4-methoxycyclohexyl]-1,4-benzodioxane-2-methanamine hemifumarate;

(±)-Cis-N-[4-(1,3-benzodioxol-5-yl)-4-ethoxycyclohexyl]-1,4-benzodioxane-2-methanamine fumarate;

(±)-Cis-N-[4-(1,3-benzodioxol-5-yl)-4-methoxycyclohexyl]-1,4-benzodioxane-2-methanamine hemifumarate;

(±)-Cis-N-ethyl-N-[4-(1,3-benzodioxol-5-yl)-4-hydroxycyclohexyl]-1,4-benzodioxane-2-methanamine fumarate;

(±)-Cis-N-methyl-N-[4-(1,3-benzodioxol-5-yl)-4-methoxycyclohexyl]-1,4-benzodioxane-2-methanamine fumarate;

(−)-(R)-Cis-N-[4-1,3-benzodioxol-5-yl)-4-methoxycyclohexyl]-1,4-benzodioxane-2-methanamine fumarate;

(±)-Trans-N-[4-1,3-benzodioxol-5-yl)-4-methoxycyclohexyl]-2S-1,4-benzodioxane-2 -methanaminehemifumarate;

N-[4-(1,3-Benzodioxol-5-yl)-3-cyclohexen-1-yl]-2S-1,4-benzodioxane-2-methanamine; and (±)-Cis-4-[(1,4-benzodioxan-2-yl)methylamino]-1-(3,4-difluorophenyl) cyclohexanol.

5. A pharmaceutical composition comprising an effective anxiolytic amount of a compound of claim 1 and a pharmaceutically acceptable carrier.

6. The composition of claim 5 wherein the compound is selected from the group consisting of:

Z-4-[2S 1,4-benzodioxan-2-yl)methylamino]-1-(1,3-benzodioxol-5-yl)cyclohexanol;

Z-N-[4-(1,3-benzodioxol-5-yl)-4-methoxycyclohexyl]-2S-1,4-benzodioxane-2-methanamine hemifumarate;

(±)-Cis-4-[[(1,4-benzodioxan-2-yl)methyl]-amino]-1-(1,3-benzodioxol-5-yl)cyclohexanol hydrate;

(±)-Cis-N-[4-(1,3-benzodioxan-6-yl)-4-methoxycyclohexyl]-1,4-benzodioxane-2-methanamine hemifumarate;

(±)-Cis-N-[4-(1,3-benzodioxol-5-yl)-4-ethoxycyclohexyl]-1,4-benzodioxane-2-methanamine fumarate;

(±)-Cis-N-[4-(1,3-benzodioxol-5-yl)-4-methoxycyclohexyl]-1,4-benzodioxane-2-methanamine hemifumarate;

(±)-Cis-N-ethyl-N-[4-(1,3-benzodioxol-5-yl)-4-hydroxycyclohexyl]-1,4-benzodioxane-2-methanamine fumarate;

(±)-Cis-N-methyl-N-[4-(1,3-benzodioxol-5-yl)-4-methoxycyclohexyl]-1,4-benzodioxane-2-methanamine fumarate;

(−)-(R)-Cis-N-[4-1,3-benzodioxol-5-yl)-4-methoxycyclohexyl]-1,4-benzodioxane-2-methanamine fumarate;

(±)-Trans-N-[4-1,3-benzodioxol-5-yl)-4-methoxycyclohexyl]-2S-1,4-benzodioxane-2-methamine hemifumarate;

N-[4-(1,3-Benzodioxol-5-yl)-3-cyclohexen-1-yl]-2S-1,4-benzodioxane-2-methanamine; and (±)-Cis-4-[(1,4-benzodioxan-2-yl)methylamino]-1-(3,4-difluorophenyl) cyclohexanol.

7. A method of treating anxiety comprising administering to a patient in need thereof an effective amount of a compound of claim 1.

8. The method of claim 7 wherein the compound is selected from the group consisting of:

Z-4-[2S-1,4-benzodioxan-2-yl)methylamino]-1-(1,3-benzodioxol-5-yl)cyclohexanol;

Z-N-[4-(1,3-benzodioxol-5-yl)-4-methoxycyclohexyl]-2S-1,4-benzodioxane-2-methanamine hemifumarate;

(±)-Cis-4-[[(1,4-benzodioxan-2-yl)methyl]-amino]-1-(1,3-benzodioxol-5-yl)cyclohexanol hydrate;

(±)-Cis-N-[4-(1,3-benzodioxan-6-yl)-4-methoxycyclohexyl]-1,4-benzodioxane-2-methanamine hemifumarate;

(±)-Cis-N-[4-(1,3-benzodioxol-5-yl)-4-ethoxycyclohexyl]-1,4-benzodioxane-2-methanamine fumarate;

(±)-Cis-N-[4-(1,3-benzodioxol-5-yl)-4-methoxycyclohexyl]-1,4-benzodioxane-2-methanamine hemifumarate;

(±)-Cis-N-ethyl-N-[4-(1,3-benzodioxol-5-yl)-4-hydroxycyclohexyl]-1,4-benzodioxane-2-methanamine fumarate;

(±)-Cis-N-methyl-N-[4-(1,3-benzodioxol-5-yl)-4-methoxycyclohexyl]-1,4-benzodioxane-2-methanamine fumarate;

(−)-(R)-Cis-N-[4-1,3-benzodioxol-5-yl)-4-methoxycyclohexyl]-1,4-benzodioxane-2-methanamine fumarate;

(±)-Trans-N-[4-1,3-benzodioxol-5-yl)-4-methoxycyclohexyl]-2S-1,4-benzodioxane-methamine hemifumarate;

N-[4-(1,3-benzodioxol-5-yl)-3-cyclohexen-1-yl]-2S-1,4-benzodioxane-2-methanamine; and (±)-Cis-4-[(1,4-benzodioxan-2-yl)methylamino]-1-(3,4-difluorophenyl) cyclohexanol.

* * * * *